United States Patent [19]
Johnson et al.

[11] Patent Number: 5,283,268
[45] Date of Patent: Feb. 1, 1994

[54] COMPOUNDS FOR THE TREATMENT OF INFLAMMATION AND ALLERGY

[75] Inventors: Malcolm Johnson; Clifford J. Whelan, both of Ware, Great Britain

[73] Assignee: Glaxo Group Limited, London, England

[21] Appl. No.: 846,011

[22] Filed: Mar. 4, 1992

[30] Foreign Application Priority Data

Mar. 5, 1991 [GB] United Kingdom ............... 9104650

[51] Int. Cl.$^5$ ............................................. A61K 31/44
[52] U.S. Cl. ..................................... 514/357; 514/826
[58] Field of Search ............................ 514/357, 826

[56] References Cited

U.S. PATENT DOCUMENTS 4,937,251 6/1990 Lunts ................................... 514/351

FOREIGN PATENT DOCUMENTS 2187734A 9/1987 United Kingdom .

OTHER PUBLICATIONS

Butchers et al., *Br. J. Pharmac.*, 71, 663–667, 1980.
Howarth et al., *Am. Rev. Resp. Dis.*, 132, 986–992, 1985.
Butchers et al., *Br. J. Pharmacol.*, 92, 745P, 1987.
Anonymous, *Doctor*, 73, Feb. 23, 1989.
Anonymous, *Hospital Doctor*, C9(10), 35, 1989.
Anonymous, *Mims Magazine*, 16, Mar. 15, 1989.
Deuchar, *Pulse*, 14, Oct. 1986.
Anonymous, *Doctor*, 36, Nov. 19, 1989.
Johnson et al., *Eur. Resp. J.*, 2(suppl. 8), 676s, abst. no. 201, 1989.
Johnson, *Eur. Resp. J.*, 2(suppl. 8), 755s, abst. no. 561a, 1989.
Anonymous, *Pharm. J.*, 244(6579), 414, Apr. 7, 1990.
Baker et al., *Am. Rev. Resp. Dis.*, 141 (4 pt 2), May 20–24, 1990.

*Primary Examiner*—Leonard Schenkman
*Attorney, Agent, or Firm*—Bacon & Thomas

[57] ABSTRACT

The present invention provides a new medical use for the dichloroaniline 4-amino-3,5-dichloro-α-[[[6-[2-(2-pyridinyl)ethoxy]hexyl]amino]methyl]benzenemethanol and its enantiomers, and physiologically acceptable salts and solvates thereof in the treatment of inflammation, allergy and allergic reaction.

7 Claims, 6 Drawing Sheets

COMPOUNDS FOR THE TREATMENT OF INFLAMMATION AND ALLERGY

This invention relates to a new medical use for the dichloroaniline compound 4-amino-3,5-dichloro-α-[[[6-[2-(2-pyridinyl)ethoxy]hexyl]amino]methyl]benzenemethanol, physiologically acceptable salts and solvates thereof and pharmaceutical compositions containing them which are disclosed in published UK Patent Specification No. 2187734A, in the treatment of inflammation, allergy, and allergic reaction.

Acute inflammation is the result of a number of processes including the activation of inflammatory cells and their accumulation in tissues; the local release of pro-inflammatory and chemotactic mediators; and vascular permeability changes which lead to plasma protein extravasation (PPE) and oedema formation.

One particular clinical condition with which inflammatory processes are associated is bronchial asthma. As reported by S. T. Holgate, Postgrad. Med. J., 64, 82–95 (1988), bronchial asthma is a multifactorial disease characterised by episodic bronchoconstriction, airway hyper-reactivity, inflammation and mucus abnormalities.

To date, bronchial asthma has been treated by combination therapy, using selective $\beta_2$-stimulants such as salbutamol to control bronchospasm and steroidal drugs such as beclomethasone dipropionate to control the inflammatory condition. $\beta_2$-adrenoreceptor agonists including salbutamol have been reported to exhibit inhibitory effects on inflammatory mediator release (see, for instance, P. R. Butchers et, al., Br. J. Pharmac., 71, 663–667 (1980) and P. H. Howarth et al., Am. Rev Resp. Dis., 132, 985–992 (1985)), however, $\beta_2$-adrenoreceptor agonists are not widely recognised as having significant clinical anti-inflammatory properties. Furthermore, such $\beta_2$-stimulants do not inhibit the so-called late asthmatic response which is classically observed some three to five hours after allergen exposure following recovery from the early asthmatic response. The late asthmatic response is not alleviated by treatment with conventional $\beta_2$-stimulants.

Published UK Patent Specification No. 2187734A discloses compounds which may be represented by the formula (I)

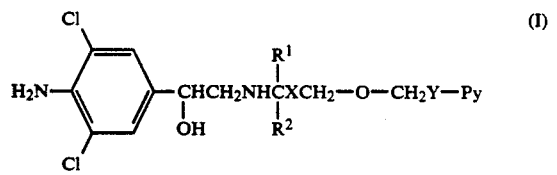

wherein

X represents a bond or a $C_{1-6}$alkylene, $C_{2-6}$alkenylene or $C_{2-6}$alkynylene chain;

Y represents a bond or a $C_{1-4}$alkylene, $C_{2-4}$alkenylene or $C_{2-4}$alkynylene chain with the proviso that the sum total of carbon atoms in X and Y is not more than 8;

Py represents a pyridinyl group optionally substituted by one or two substituents selected from halogen atoms, or hydroxy, $C_{1-3}$alkyl or $C_{1-3}$alkoxy groups; and $R^1$ and $R^2$ each represents a hydrogen atom or $C_{1-3}$alkyl group with the proviso that the sum total of carbon atoms in $R^1$ and $R^2$ is not more than 4; and physiologically acceptable salts and solvates (e.g. hydrates) thereof.

Suitable physiologically acceptable salts of the compounds of general formula (I) include acid addition salts derived from inorganic and organic acids, such as hydrochlorides, hydrobromides, sulphates, phosphates, maleates, tartrates, citrates, benzoates, 4-methoxybenzoates, 2- or 4-hydroxybenzoates, 4-chlorobenzoates, benzenesulphonates, p-toluenesulphonates, methanesulphonates, naphthalenesulphonates, fumarates, succinates, lactates, glutarates, gluconates, tricarballylates, hydroxy-naphthalenecarboxylates e.g. 1-hydroxy-or 3-hydroxy-2-naphthalenecarboxylates, or oleates.

A preferred compound of formula (I) for use according to the present invention is 4-amino-3,5-dichloro-α-[[[6-[2-(2-pyridinyl) ethoxy]hexyl]amino]methyl]benzenemethanol, hereinafter referred to as "Compound A", which may be represented by the formula (Ia)

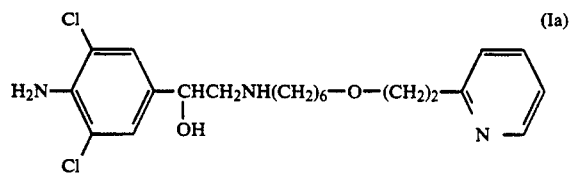

and its physiologically acceptable salts and solvates.

Compound A is preferably administered in the form of its fumarate salt preferably, its z:1 fumarate salt.

The compounds disclosed in the aforementioned patent specification are described as selective $\beta_2$-adrenoreceptor agonists having a long duration of action which are particularly useful in the treatment of diseases associated with reversible airways obstruction, such as asthma and chronic bronchitis.

We have now found that contrary to the general findings for $\beta_2$-adrenoreceptor agonists, the compounds of formula (I) exhibit a significant anti-inflammatory activity in vivo over a prolonged period such that the compounds of formula (I) are effective in the treatment of the inflammatory component of bronchial asthma.

By virtue of its anti-inflammatory activity, Compound A or a physiologically acceptable salt or solvate thereof may be used in the treatment of a mammal, including man, suffering from pulmonary inflammation including alveolar inflammation and inflammation of the respiratory airways. In particular, Compound A or a physiologically acceptable salt or solvate thereof is useful in the treatment of inflammation associated with pulmonary diseases such as asthma and chronic bronchitis, emphysema, cystic fibrosis and adult respiratory distress syndrome (ARDS).

Compound A or a physiologically acceptable salt or solvate thereof may also be used in the treatment of a mammal, including man, suffering from pulmonary inflammation associated with the late asthmatic response.

Additionally, Compound A or a physiologically acceptable salt or solvate thereof may be used in the treatment of a mammal, including man, suffering from an allergy or allergic reaction such as allergic rhinitis, contact dermatitis, allergic conjunctivitis and the like or an inflammatory condition such as episcleritis, tendinitis, rheumatoid opondylitis, osteoarthritis, gouty arthritis and other arthritic conditions.

Compound A or a physiologically acceptable salt or solvate thereof is particularly useful in the treatment of inflammatory and allergic skin diseases such as, for example, urticaria, psoriasis, eczema and atopic dermatitis.

Compound A or a physiologically acceptable salt or solvate thereof may also be used in the treatment of a mammal, including man, suffering from inflammation of the gastrointestinal tract. Such conditions may be for example, ulcerative colitis, Crohn's disease, damage caused by non-steroidal drugs, and inflammatory bowel disease.

According to one aspect of the invention we therefore provide a therapeutic agent comprising as active ingredient Compound A or a physiologically acceptable salt or solvate thereof for use in treating, relieving or preventing the effects of inflammation, allergy, or allergic reaction.

In an alternative or further aspect the invention provides a method of treatment of a mammal, including man, suffering from or susceptible to the effects of inflammation, allergy or allergic reaction which comprises administering an effective amount of Compound A or a physiologically acceptable salt or solvate thereof. It will be appreciated that whilst Compound A will primarily be of use in the alleviation of established symptoms, prophylaxis is not excluded.

In a further aspect, the invention provides Compound A or a physiologically acceptable salt or solvate thereof for use in the manufacture of a medicament for treating relieving or preventing the effects of inflammation, allergy, or allergic reaction.

A particularly preferred compound for use in accordance with the present invention is the (R) enantiomer of Compound A or a physiologically acceptable salt or solvate thereof.

Preparation of the (R) and (S) enantiomers of Compound A is described in European Patent Specification No. 0460924, the contents of which are incorporated herein by way of reference.

The anti-inflammatory activity of Compound A in the lung was assessed by investigating the effect of the drug on inflammatory mediator release in human lung tissues in vitro, and on inflammatory cell infiltration and accumulation, and vascular permeability and plasma protein extravasation in the airway lumen of the guinea-pig in vivo (see Example 1, below).

The anti-inflammatory activity of the Compound A in the skin was assessed by investigating the effect of the drug on plasma protein extravasation (PPE) as a measure of vascular permeability (see Example 2, below).

Thus, in an alternative or further aspect the invention provides Compound A or a physiologically acceptable salt or solvate thereof for use in treating, relieving or preventing a disease involving inflammatory cell accumulation in the lungs.

Additionally the invention provides Compound A or a physiologically acceptable salt or solvate thereof for use in treating, relieving or preventing a disease involving increased vascular permeability and plasma protein extravasation in the lungs.

The invention further provides Compound A or a physiologically acceptable salt or solvate thereof for use in treating, relieving or preventing a disease involving granulocyte accumulation in the skin.

The invention still further provides Compound A or a physiologically acceptable salt or solvate thereof for use in treating, relieving or preventing a disease involving increased vascular permeability in the skin.

As used herein, the term "increased vascular permeability" is intended to refer to elevated levels of vascular permeability with respect to those generally observed in a healthy individual.

Figure 1:
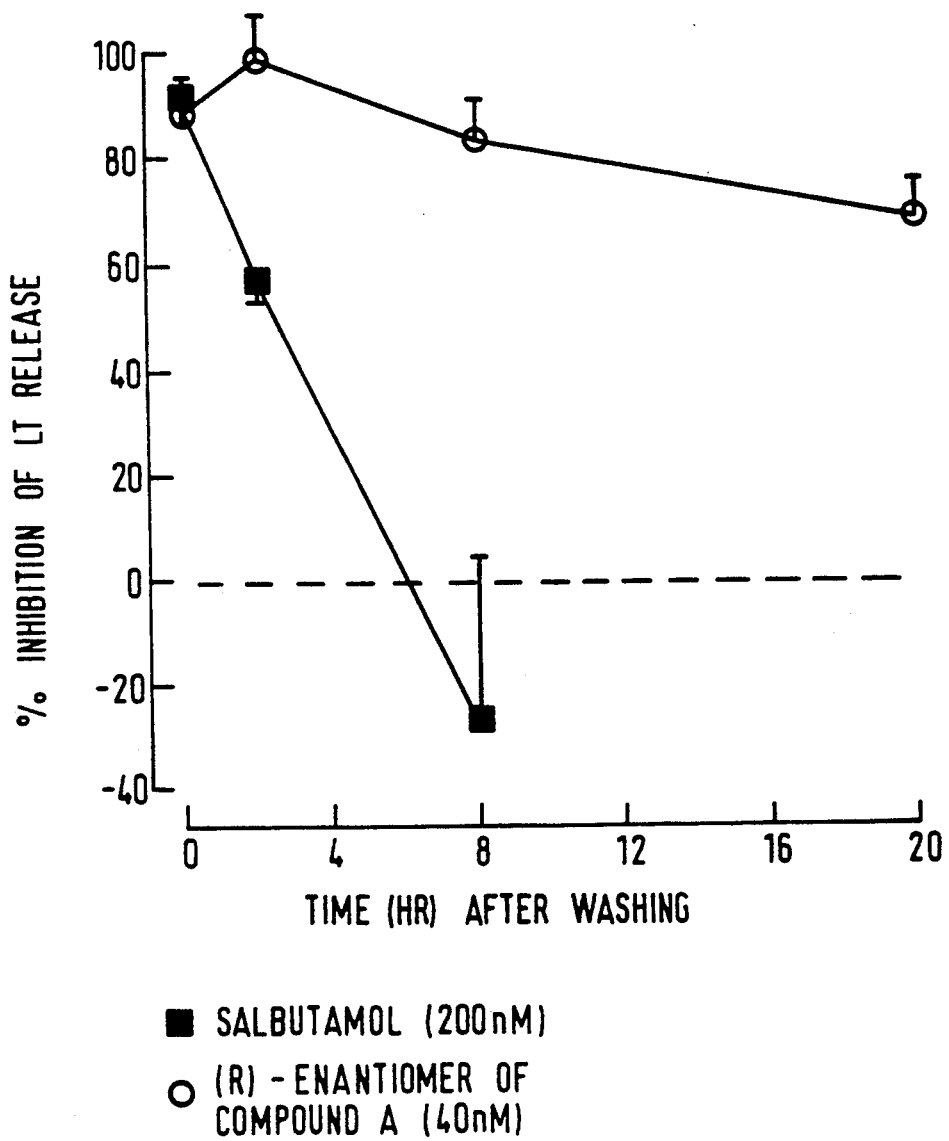
FIG. 1 shows a comparison of the inhibition by the (R)-enantiomer of Compound A and salbutamol of leukotriene release from human lung tissue fragments in vitro.

While it is possible for Compound A to be administered alone as the raw chemical, it is preferable to present the active ingredient as a pharmaceutical formulation. Formulations of Compound A for use according to the invention, both for veterinary and for human medical use, comprise the active compound together with one or more pharmaceutically acceptable carriers and optionally any other therapeutic ingredients. The carriers must be pharmaceutically acceptable in the sense of being compatible with the other ingredients of the formulation and not deleterious to the recipient thereof. The other therapeutic ingredients may include analgesics, such as aspirin or codeine, anti-pyretics, or other anti-inflammatories.

Compound A for use according to the invention may be formulated in a conventional manner for administration by any convenient route, for example for administration by inhalation or insufflation, or for oral, buccal, parenteral, topical (including nasal) or rectal administration.

For administration by inhalation the compound for use according to the invention is conveniently delivered in the form of an aerosol spray presentation from pressurised packs, with the use of a suitable propellants such as dichlorodifluoromethane, trichlorofluoromethane, dichlorotetrafluoroethane, carbon dioxide or other suitable gas, or from a nebuliser. In the case of a pressurised aerosol the dosage unit may be determined by providing a valve to deliver a metered amount.

Alternatively, for administration by inhalation or insufflation, Compound A may take the form of a dry powder composition, for example a powder mix of the compound and a suitable powder base such a lactose or starch. The powder composition may be presented in unit dosage form in, for example, capsules or cartridges of e.g. gelatin, or blister packs from which the powder may be administered with the aid of an inhaler or insufflator.

For oral administration, the pharmaceutical composition may take the form of, for example, tablets, capsules, powders, solutions, syrups or suspensions prepared by conventional means with acceptable excipients.

For buccal administration the composition may take the form of tablets, drops or lozenges formulated in a conventional a manner.

Compound A may be formulated for parenteral administration. Formulations for injections may be presented in unit form in ampoules, or multi-dose containers with an added preservative. The compositions may take such forms as suspensions, solutions or emulsions in oily or aqueous vehicles, and may contain formulatory agents such as suspending, stabilising and or dispersing agents. Alternatively, the active ingredient may be in powder form for reconstitution with a suitable vehicle, e.g sterile pyrogen-free water, before use.

For topical administration the pharmaceutical composition may take the form of ointments, lotions or creams formulated in a conventional manner, with for example an aqueous oily base, generally with the addition of suitable thickening agents and or solvents. For nasal application, the composition may take the form of a spray, formulated for example as an aqueous solution or suspension or as an aerosol with the use of a suitable propellant.

Compound A may also be formulated in rectal compositions such as suppositories or retention enemas, e.g containing conventional suppository bases such as cocoa butter or other glycerides.

Where pharmaceutical compositions are described above for oral, buccal, rectal or topical administration, these may be presented in a conventional manner associated with controlled release forms.

A proposed daily dosage of active compound for the treatment of man is 0.0005 mg to 100 mg, which may be conveniently administered in one or two doses. The precise dose employed will of course depend on the age and condition of the patient and on the route of administration. Thus a suitable dose for administration by inhalation is 0.0005 mg to 10 mg, for oral administation is 0.02 mg to 100 mg, and for parenteral administration is 0.001 mg to 2 mg.

The following are examples of suitable formulations for use in invention. The term "active ingredient" is used herein to represent Compound A.

Tablets

These may be prepared by the normal methods such as wet granulation or direct compression.

A. Direct Compression

|  | mg/tablet |
| --- | --- |
| Active ingredient | 2.0 |
| Microcrystalline Cellulose USP | 196.5 |
| Magnesium Stearate BP | 1.5 |
| Compression weight | 200.0 |

The active ingredient is sieved through a suitable sieve, blended with the excipients and compressed using 7 mm diameter punches.

Tablets of other strengths may be prepared by altering the ratio of active ingredient to microcrystalline cellulose or the compression weight and using punches to suit.

B. Wet Granulation

|  | mg/tablet |
| --- | --- |
| Active ingredient | 2.0 |
| Lactose BP | 151.5 |
| Starch BP | 30.0 |
| Pregelatinised Maize Starch BP | 15.0 |
| Magnesium Stearate BP | 1.5 |
| Compression weight | 200.0 |

The active ingredient is sieved through a suitable sieve and blended with lactose, starch and pregelatinised maize starch. Suitable volumes of purified water are added and the powders are granulated. After drying, the granules are then compressed into tablets using 7 mm diameter punches. Tablets of other strengths may be prepared by altering the ratio of active ingredient to lactose or the compression weight and using punches to suit.

Injection for intravenous Administration

|  | mg/ml |
| --- | --- |
| Active ingredient | 0.5 mg |
| Sodium Chloride BP | as required |
| Water for injection BP to | 1.0 ml |

Sodium chloride may be added to adjust the tonicity of the solution and the pH may be adjusted, using acid or alkali, to that of optimum stability and/or facilitate solution of the active ingredient. Alternatively suitable buffer salts may be used.

The solution is prepared, clarified and filled into appropriate size ampoules sealed by fusion of the glass. The injection is sterilised by heating in an autoclave using one of the acceptable cycles. Alternatively the solution may be sterilised by filtration and filled into sterile ampoules under acceptable conditions. The solution may be packed under an inert atmosphere of nitrogen or other suitable gas.

Metered Dose Pressurised Aerosol

A. Suspension Aerosol

|  | mg/metered dose | per can |
| --- | --- | --- |
| Active ingredient micronised | 0.100 | 26.40 mg |
| Oleic Acid BP | 0.010 | 2.64 mg |
| Trichlorofluoromethane BP | 23.64 | 5.67 g |
| Dichlorodifluoromethane BP | 51.25 | 14.70 g |

The active ingredient is micronised in a fluid energy mill to a fine particle size range, The oleic acid is mixed with the trichloroflurormethane at a temperature of 10°-15° C. and the micronised drug is mixed into the solution with a high shear mixer. The suspension is metered into aluminium aerosol cans and suitable metering valves, delivering 85 mg of suspension are crimped onto the cans and the dichlorodifluoromethane is pressure filled into the cans through the valves.

B. Solution Aerosol

|  | mg/metered dose | per can |
| --- | --- | --- |
| Active ingredient | 0.100 | 24.0 mg |
| Ethanol BP | 7.500 | 1.80 g |
| Trichlorofluoromethane BP | 18.875 | 4.53 g |
| Dichlorodifluoromethane BP | 48.525 | 11.65 g |

Oleic acid BP, or a suitable surfactant e.g. Span 85 (sorbitan trioleate) may also be included.

The active ingredient is dissolved in the ethanol together with the oleic acid or surfactant if used. the alcoholic solution is metered into suitable aerosol containers followed by the trichlorofluoromethane. Suitable metering valves are crimped onto the containers and dichlorodifluoromethane is pressure filled into them through the valves.

The following examples illustrate the studies demonstrating the potent and long-acting anti-inflammatory activity effect of Compound A in the lung and in the skin.

The following abbreviation are used in: LPS-lipopolysaccharide; PAF-platalet activating factor; BALF-bronchoalveolar fluid; PPE-plasma protein extravasation; PMN-guinea pig peritoneal neutrophil.

EXAMPLE 1

ANTI-INFLAMMATORY ACTIVITY IN THE LUNG (i) Inflammatory Mediator Release

The effect of $\beta_2$-adrenoreceptor agonists on inflammatory mediator release was evaluated using the method of Butchers et al Br.J.Pharmac., 67, 23-32 (1979).

Briefly, human lung fragments were sensitised by incubation overnight at 20° C. in serum from an allergic donor. The lung fragments were then pre-incubated with varying concentrations (0.3-300 nM) of $\beta_2$-adrenoreceptor agonists for 30 min. before being challenged with specific antigen. The supernatants were assayed for mediator release, (leukotriene $C_4$, $D_4$, and $E_4$) by radio-immunoassay (Amersham, UK). Inhibition of mediator release was calculated as described by Butchers et al (1979) supra.

To compare the duration of action of $\beta_2$-agonists, sensitised human lung fragments were pre-incubated with a single concentration of compound sufficient to cause just maximum inhibition of mediator release. The fragments were then washed and incubated in a large volume of Tyrode's solution at 37° C. Aliquots were removed at varying time intervals (0-20 h), challenged with antigen and mediator release measured as described above.

The racemate of Compound A (0.1-10 nM), the (R) enantiomer of Compound A (0.1-10 nM) and the (S) enantiomer of Compound A (0.1-10 nM) caused a concentration-dependent inhibition of mediator release (leukotriene $C_4/D_4/E_4$) from human lung fragments with $IC_{50}$'s of 0.5-1.5 nM, 0.1-1.0 nM and 5.0-10 nM, respectively. Salbutamol in similar experiments has an $IC_{50}$ of 10-50 nM.

Inhibition of leukotriene release by Compound A (40 nM) was sustained, significant inhibitory activity still being observed after 20 h (FIG. 1). In contrast, the effect of an equipotent concentration of salbutamol (200 nM) was poorly maintained, with loss of inhibitory activity within 2-4 h (FIG. 1).

(ii) Inflammatory cell Accumulation

Guinea-pigs (Dunkin-Hartley, 200 g) were sensitized by two intraperitoneal injections of 10 μg ovalbumin two weeks apart (Sanjar et al, Br. J. Pharmacol., 99, 679-686, 1990).

Two weeks later the animals were exposed to aerosols derived from solutions of the (R) enantiomer of Compound A (12 mM) or vehicle for 15 min. prior to antigen challenge. The antigen challenge was an aerosol of 0.005% ovalbumin in phosphate-buffered saline given for 30 min. The animals were predosed with mepyramine (1 mg/kg i.p.) to prevent terminal bronchoconstriction. The animals were killed 24 hr later and bronchial lavage performed.

The total numbers of leucocytes in the bronchoalveolar (BAL) fluid recovered was determined using a Medonic CA480 cell analyser. Numbers of eosinophils were calculated from differential cell counts carried out after staining in Leishmann's solution.

Although the lungs of unchallenged animals contain eosinophils, antigen challenge caused an approximate 4-fold increase in the number of eosinophils recovered in BAL fluid (table 1). Pretreatment of the animals with the (R) enantiomer of Compound A inhibited this response to antigen by about 60%.

TABLE 1

| EOSINOPHILS $\times 10^5$/ml BAL FLUID | |
|---|---|
| Unchallenged | 1.69 ± 0.47 |
| Challenged | 7.22 ± 1.42 |
| Challenged +(R) enantiomer of Compound A (12 mM) | 3.85 ± 1.80 |

Data are expressed as means ± s.e. mean of 4 animals/group.

(iii) Vascular Permeability and Plasma Protein Extravasation

The method of evaluating the effects of $\beta_2$-adrenoreceptor agonists on vascular permeability and plasma protein extravasation was adapted from the technique of Erjefalt et al Acta.Physiol.Scand., 128, 653-654 (1986).

Briefly, guinea-pigs (male Dunkin Hartley, 300-400 g) were given an intracardiac injection of iodinated human serum albumin (0.5 μCi) in heparinised saline (10 U.ml$^{-1}$). Animals were then exposed to an aerosol of histamine (0.5 mg.ml$^{-1}$) generated by a Devilbiss nebuliser for 30 sec, followed by a further 30 sec exposure to the atmosphere in the chamber. Thirty minutes after histamine challenge, a blood sample was taken and the lungs lavaged twice with 10 ml heparinised (10 U.ml$^{-1}$) phosphate-buffered saline at 37° C. The radioactivity in both an aliquot of plasma and in a 5 ml sample of the pooled bronchoalveolar lavage fluid (BALF) was measured. Plasma protein extravasation (PPE; μl plasma.ml$^{-1}$ BALF) was calculated. $\beta_2$-adrenoreceptor agonists were administered by aerosol as described by Ball et al Br.J.Pharmac., 90 150P (1987), at timed intervals before histamine challenge.

Figure 2:
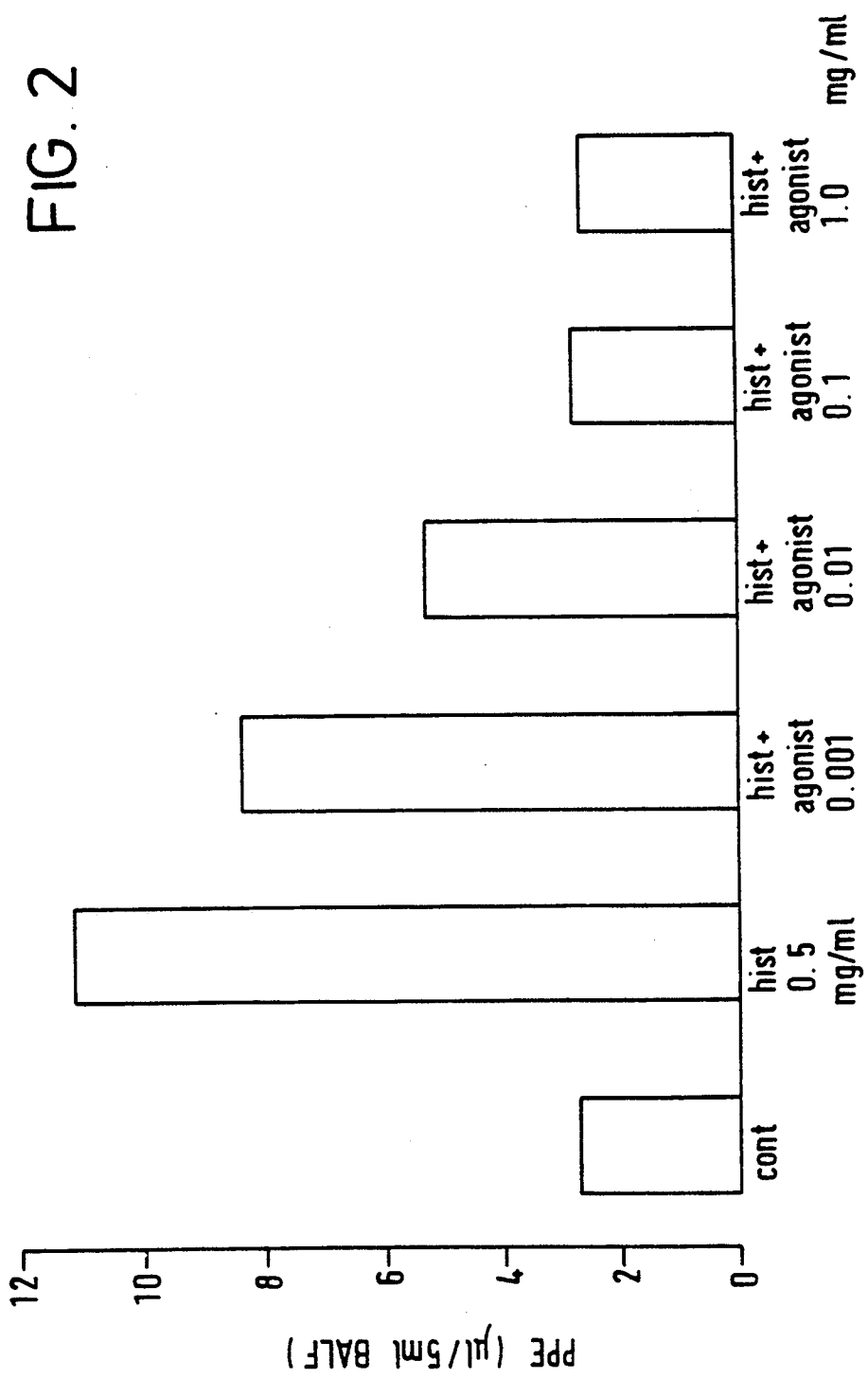
FIG. 2 shows the inhibition by the (R)-enantiomer of Compound A of histamine-induced plasma protein extravasation (PPE) in guinea pig lung in vivo.

The (R) enantiomer of Compound A (nebuliser concentration: 0.001-1 mg.ml$^{-1}$) inhibited histamine-induced PPE in a concentration-related manner, the highest doses causing complete inhibition (FIG. 2). The concentration of the (R) enantiomer of Compound A required to reduce histamine-induced PPE by 50% ($ED_{50}$) was about 0.003 mg.ml$^{-1}$.

Figure 3:
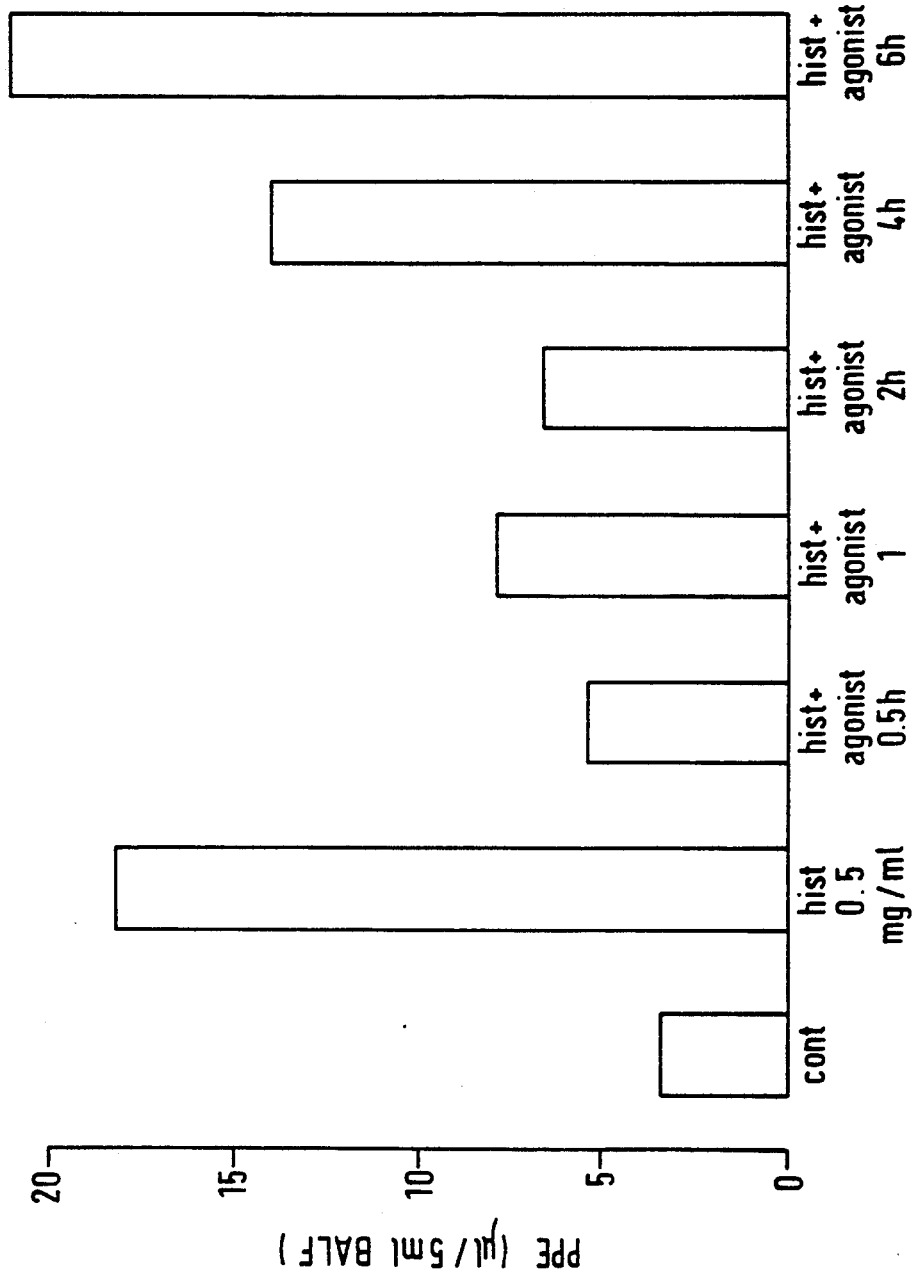
FIG. 3 shows the duration of inhibition by the (R)-enantiomer of Compound A of histamine-induced plasma protein extravasation (PPE) in guinea pig lung in vivo.
Figure 4:
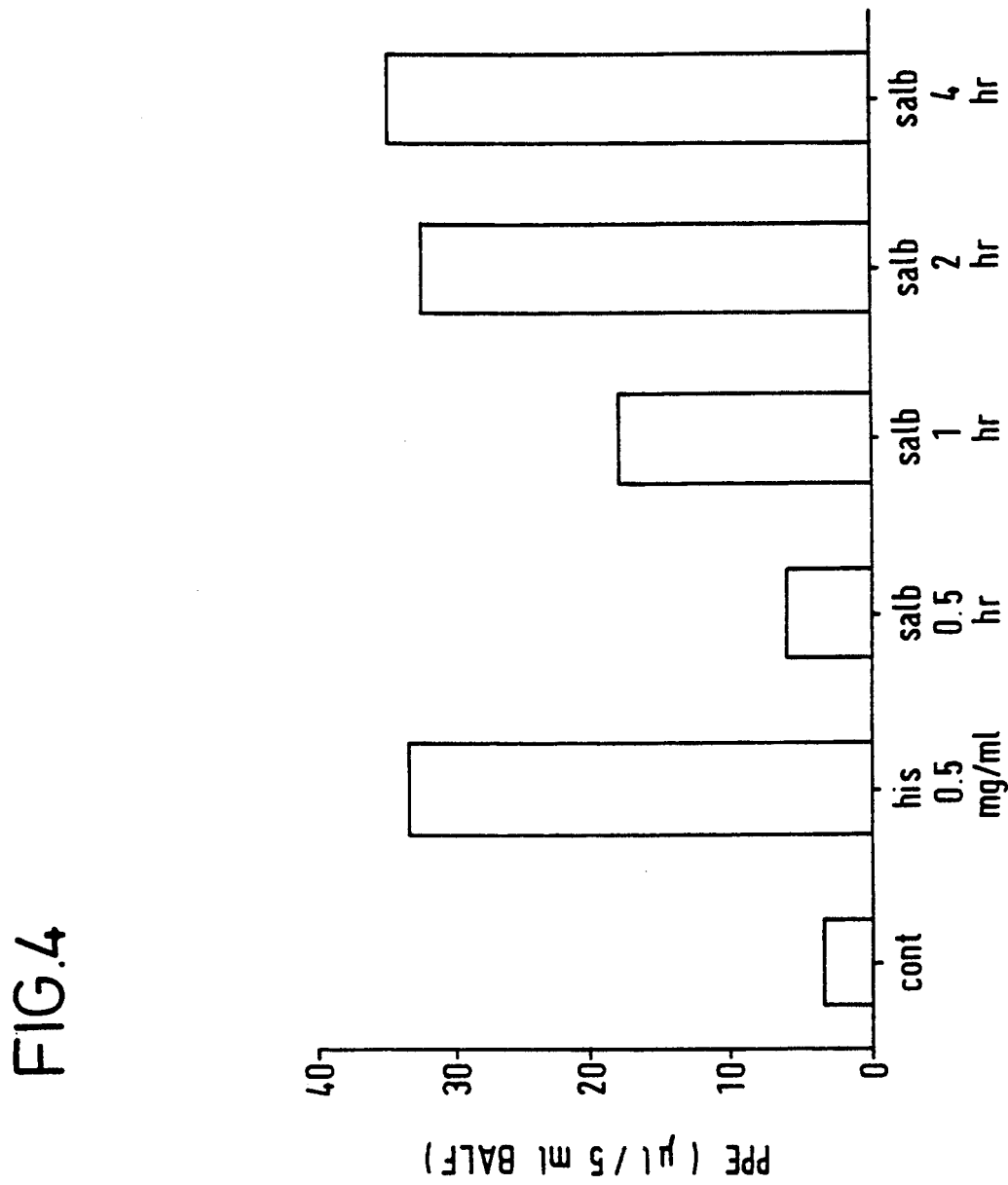
FIG. 4 shows the duration of inhibition by salbutamol of histamine-induced plasma protein extravasation (PPE) in guinea pig lung in vivo (for comparison with FIG. 3).

Inhibition of histamine induced PPE by the inhaled (R) enantiomer of Compound A was long-lasting, still being evident 4 hours after administration (FIG. 3). In contrast, at equi-effective doses, salbutamol had a shorter duration of action, with substantial loss of activity after 2 hours (FIG. 4).

EXAMPLE 2

ANTI-INFLAMMATORY ACTIVITY IN THE SKIN (i) Bradykinin-Induced Increases in Vascular Permeability Guinea-pigs were anaesthesised with ketamine/xylazine i.m. followed by an intracardiac injection of iodinated human serum albumin. Each guinea-pig received a series of intradermal injections (usually six) of sterile saline (50 μl) or β-adrenoreceptor agonist dissolved in sterile saline into the abdominal skin. Fifteen minutes later, each animal received an intradermal injection of saline (50 μl) or bradykinin ($10^{-10}$–$10^{-6}$ moles) in sterile saline into the same sites. Thus in each guinea-pig six sites were injected with either sterile saline or bradykinin following pretreatment with either sterile saline or β-adrenoreceptor agonist.

Thirty minutes later all guinea-pigs were killed with an overdose of sodium pentobarbitone, a plasma sample prepared and the skin sites removed with a hollow punch.

The iodinated albumin content of the plasma and skin biopsies was determined by scintillation counting. From these data, plasma protein extravasation, expressed as μl plasma per site, was calculated. All values for plasma protein extravasation quoted are corrected for that seen following an intradermal injection of saline.

Intradermal injection of the (R) enantiomer of Compound A ($10^{-10}$–$10^{-8}$ moles/site) did not cause plasma protein extravasation.

Figure 5:
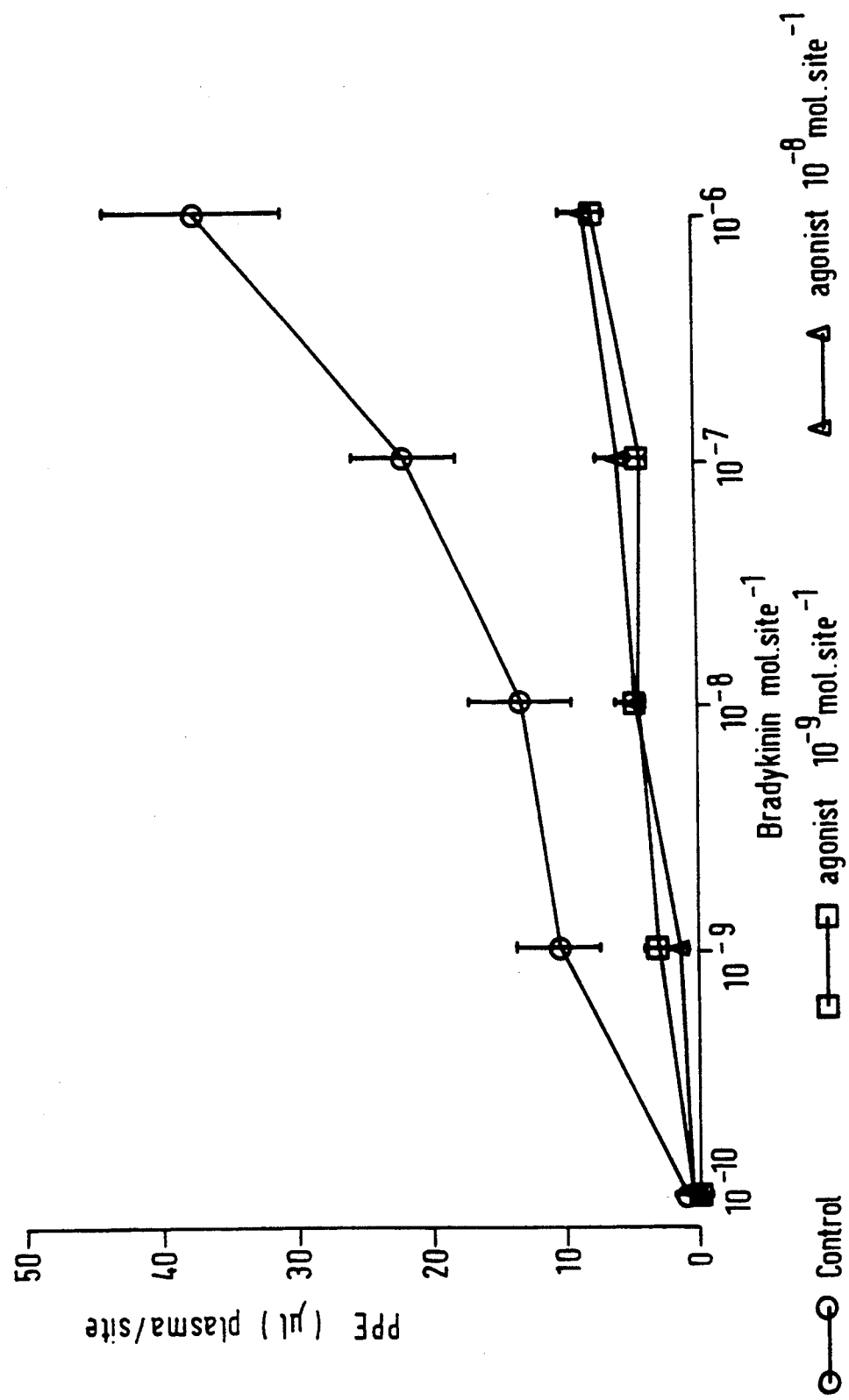
FIG. 5 shows the inhibition by the (R)-enantiomer of Compound A of bradykinin-induced plasma protein extravasation (PPE) in guinea pig skin.

Intradermal administration of the (R) enantiomer of Compound A ($10^{-9}$ and $10^{-8}$ moles/site) 15 min prior to bradykinin markedly reduced plasma protein extravasation induced by a range of doses of bradykinin (FIG. 5).

Figure 6:
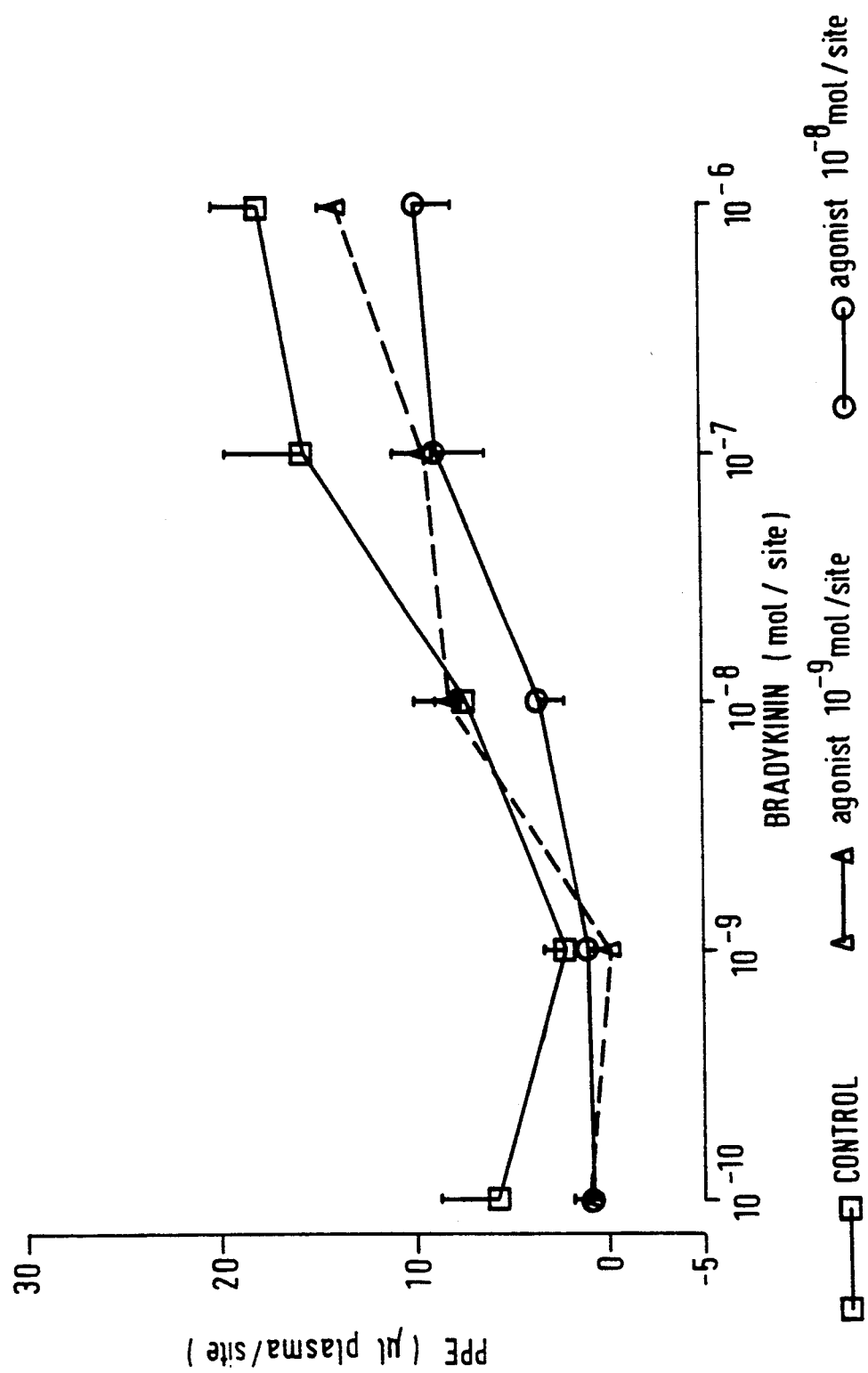
FIG. 6 shows the inhibition by the (S)-enantiomer of Compound A of bradykinin-induced plasma protein extravasation (PPE) in guinea pig skin.

The (S) enantiomer of Compound A ($10^{-9}$ and $10^{-8}$ moles/site) also inhibited bradykinin-induced PPE (FIG. 6).

We claim:

1. A method of treatment of a mammal, including man, suffering from the effects of pulmonary inflammation associated with the late asthmatic response which comprises administering an effective amount of the compound of formula (1a)

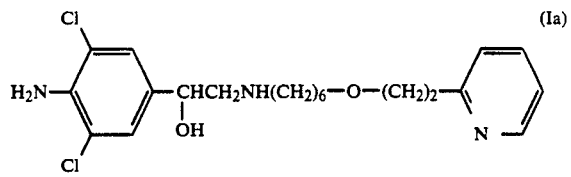

or a physiologically acceptable salt or solvate thereof.

2. A method of treatment according to claim 1 which comprises administering an effective amount of the (R)-enantiomer of the compound of formula (1a) or a physiologically acceptable salt or solvent thereof.

3. A method of treatment according to claim 1 wherein the compound of formula (1a) is in the form of its 2:1 fumarate salt.

4. A method of treatment according to claim 2 wherein the compound of formula (1a) is in the form of its 2:1 fumarate salt.

5. A method of treatment according to claim 1 wherein the compound of formula (1a) or a physiologically acceptable salt or solvate thereof is administered by inhalation or by insufflation.

6. A method of treatment according to claim 3 wherein the compound of formula (1a) or a physiologically acceptable salt or solvate thereof is administered by inhalation or by insufflation.

7. A method of treatment according to claim 4 wherein the compound of formula (1a) or a physiologically acceptable salt or solvate thereof is administered by inhalation or by insufflation.

* * * * *